United States Patent [19]
Taubenblatt

[11] Patent Number: 5,432,607
[45] Date of Patent: Jul. 11, 1995

[54] METHOD AND APPARATUS FOR INSPECTING PATTERNED THIN FILMS USING DIFFRACTED BEAM ELLIPSOMETRY

[75] Inventor: Marc A. Taubenblatt, Pleasantville, N.Y.

[73] Assignee: International Business Machines Corportion, Armonk, N.Y.

[21] Appl. No.: 21,004

[22] Filed: Feb. 22, 1993

[51] Int. Cl.⁶ .................... G01N 21/89; G02B 27/46; G06F 15/46
[52] U.S. Cl. .................... 356/364; 356/237; 356/401; 250/206.2; 250/206.1
[58] Field of Search ............... 356/364, 400, 401, 357, 356/369, 445, 301, 351, 354, 356, 237; 250/206.2, 206.1

[56] References Cited

U.S. PATENT DOCUMENTS

| | | | |
|---|---|---|---|
| 3,614,232 | 11/1968 | Mathisen | 356/71 |
| 3,741,660 | 6/1973 | Abu-Shumays et al. | 356/114 |
| 3,814,520 | 6/1974 | Baker et al. | 356/71 |
| 4,198,261 | 4/1980 | Busta et al. | 356/364 |
| 4,303,341 | 12/1981 | Kleinknecht et al. | 356/384 |
| 4,410,277 | 10/1983 | Yamamoto et al. | 356/366 |
| 4,586,819 | 5/1986 | Tochigi et al. | 356/364 |
| 4,870,674 | 9/1989 | Schmahl et al. | 378/43 |
| 4,919,536 | 4/1990 | Komine | 356/339 |
| 5,120,966 | 6/1992 | Kondo | 356/357 |
| 5,164,589 | 11/1992 | Sjödin | 356/244 |
| 5,262,644 | 11/1993 | Maguire | 356/301 |
| 5,274,434 | 12/1993 | Morioka et al. | 356/237 |

FOREIGN PATENT DOCUMENTS 63-41038  2/1988  Japan .................... 356/369

OTHER PUBLICATIONS

"Detection of thickness uniformity of film layers in semiconductor devices by spatially resolved ellipsointerferometry": by Teruhito Mishima & Kwan Kao; Optical Engineering, vol. 21(6), 1074–1078 (Nov./Dec. 1982) 1982 SPIE; pp. 549–553.

Dynamic Imaging Microellipsometry: theory, system design, & feasibility demonstration; by R. F. Cohn, J. W. Wagner, & J. Kruger; Applied Optics/vol. 27, No. 22/Nov. 15, 1988; pp. 4664–4671.

Nondestructive Mapping of Surface Film Parameters with Dynamic Imaging Microellipsometry by Ralph F. Cohn & J. W. Wagner (pp. 1219–1226; Review of Progress in Quantitative Nondestructive Evaluation; vol. 8B edited by D. O. Thompson & D. E. Chimenti; Plenum Press, N.Y. & London.

Apparatus & Techniques; "Tuning a Babinet-Soleil compensator for exact quarter wave retardation in an ellipsometer" by R. M. A. Azzam & J. A. Krueger from Journal of Physics E, vol. 8, No. 6, pp. 445–446; Jun. 1975.

"Spatially resolved ellipsometry" by M. Erman & J. B. Theeten from Journal of Applied Physics, vol. 69(3), 859–873 (Aug. 1, 1986); pp. 554–568.

"Light scattering methods for semiconductor process monitoring & control": by R. A. Gottscho, M. F. Vernon, J. A. Gregus, E. Yoon, K. P. Giapis, T. R. Hayes, W. S. Hobson, L. Clark, J. Kruskal, D. Lambert.

(List continued on next page.)

Primary Examiner—Robert P. Limanek
Assistant Examiner—Alexander Oscar Williams
Attorney, Agent, or Firm—Ratner & Prestia

[57] ABSTRACT

A method and apparatus for inspecting a repeating pattern on an object using an optical inspection system to detect variations in the pattern. The object is illuminated with substantially monochromatic light. A diffracted beam is formed. The diffracted beam has a plurality of polarization components. At least one of the polarization components of the diffracted beam is blocked. Variations in the pattern are detected as light intensity variations in the polarization components that are not blocked.

23 Claims, 5 Drawing Sheets

OTHER PUBLICATIONS

"Use of Light Scattering in Characterizing Reactively Ion Etched Profiles" by Konstantinos P. Giapis, Richard A. Gottscho, Linda A. Clark, J. B. Kruskal & Diane Lambert; from J. Vac. Sci. Technol. A, vol. 9, No. 3, May/Jun. 1991; pp. 664–668.

"Precison ellipsometry based on a focused light beam Part. 1"; by D. O. Barsukov, G. M. Gusakov, & A. A. Komarnitskii from Optics & Spectroscopy, vol. 64(6), 782–785 (Jun,. 1988); 1988 Optical Society of America; pp. 569–572.

"Analysis of Passive Film Growth by Dynamic Imaging Microellipsometry" by C. C. Streinz, J. W. Wagner, & J. Kruger from J. Electrochem, Soc., vol. 139, No. 3, Mar. 1992; The Electrochemical Society, Inc. pp. 711–715.

"A simple fourier photopolarimeter with rotating polarizer & analyzer for measuring Jones & Mueller Matrices" by R. M. A. Azzam from Optics Communications, vol. 25, No. 2, May 1978; pp. 137–140.

"Determination of the Ellipsometric Characteristics of Optical Surfaces Using Nanosecond Laser Pulses" by Edward Collett from Surface Science 96, No. 1–3 (Jun. 1980); pp. 156–167.

"Dynamic Imaging Microellipsometry" by R. F. Cohn, J. W. Wagner & Jerome Kruger from Journal of the Electrochemical Society; Apr. 1988; pp. 1033–1034.

"Ellipsometry & Polarized Light" by R. M. A. Azzam & N. M. Bashara; from Elsevier Science Publishers B.V., 1977; pp. 159, 234–235, 238–243, 246–249, & 262–263.

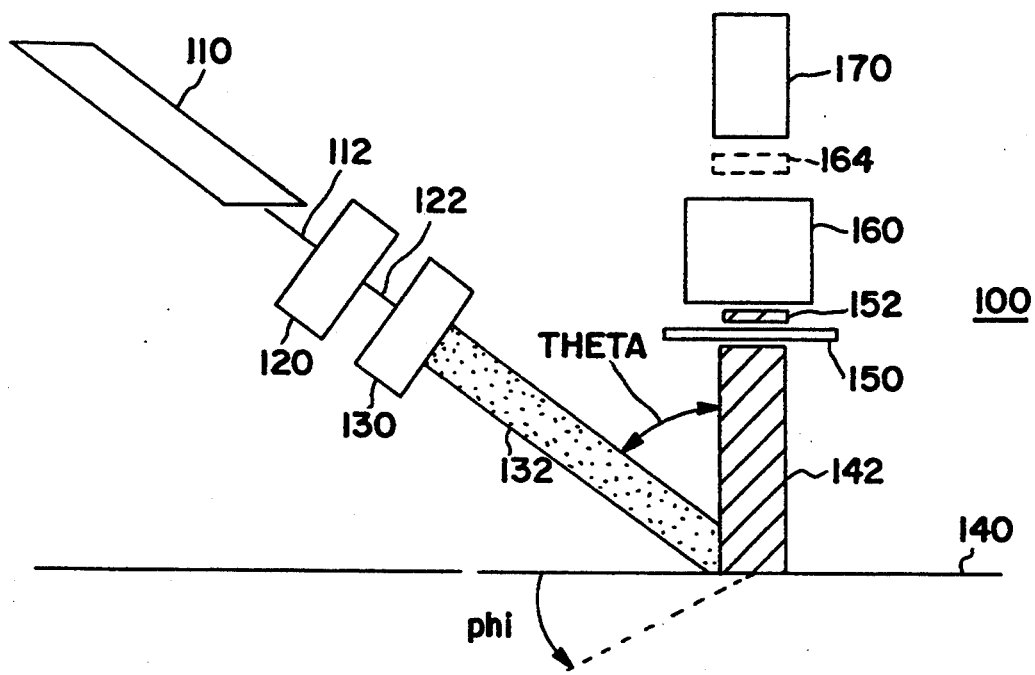
FIG.I
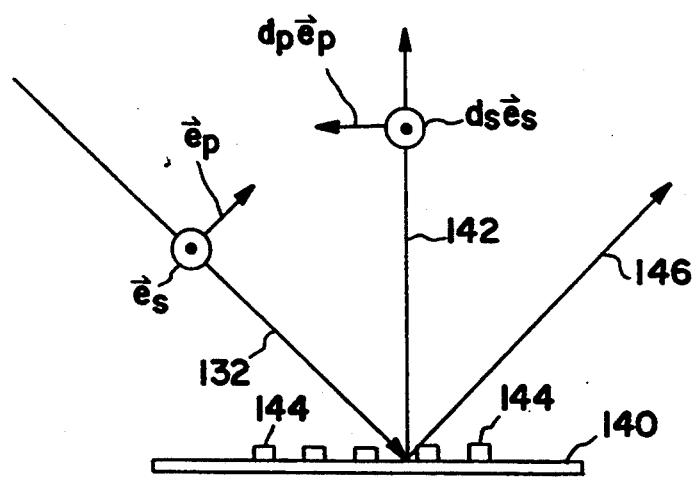
FIG.2

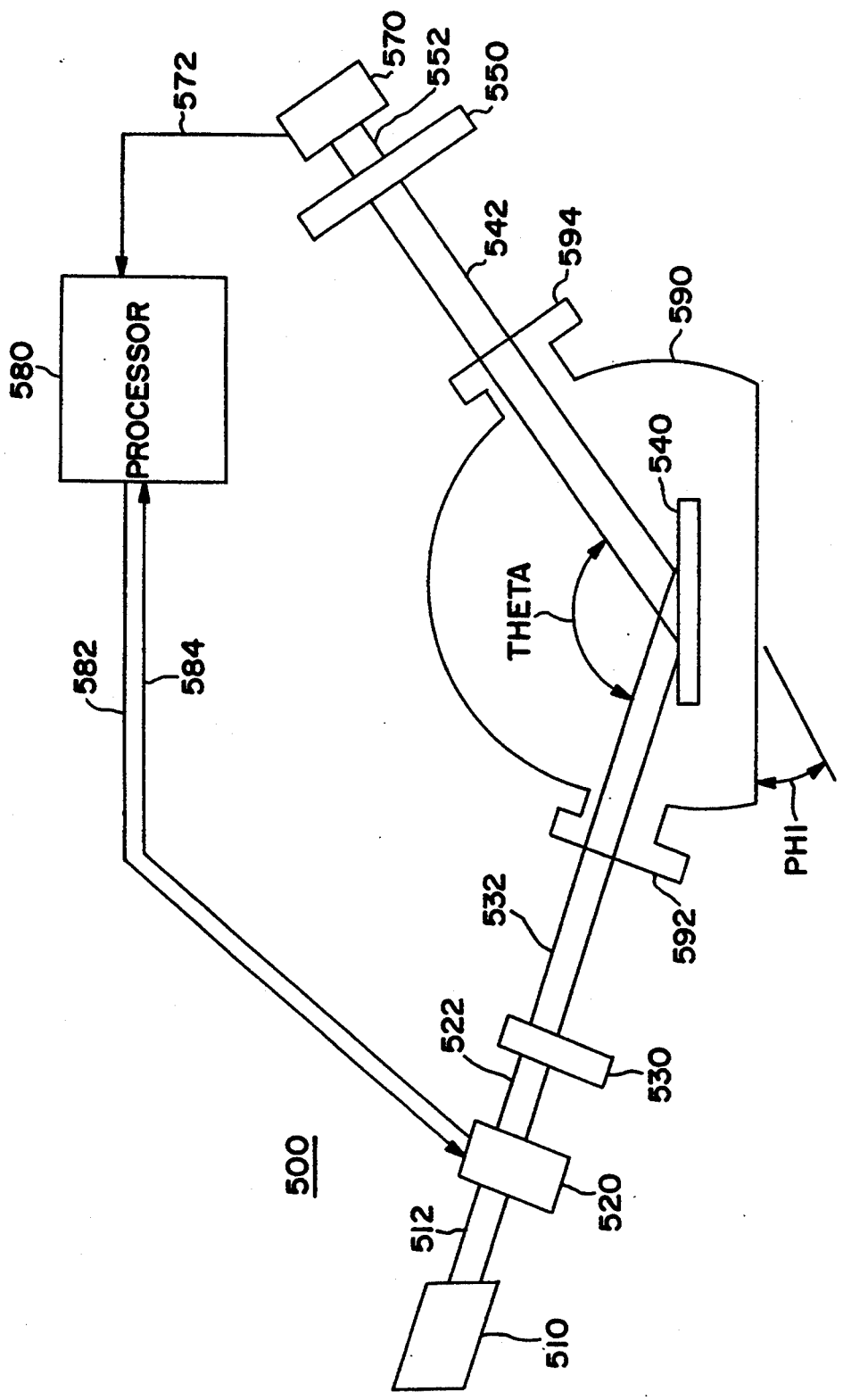

METHOD AND APPARATUS FOR INSPECTING PATTERNED THIN FILMS USING DIFFRACTED BEAM ELLIPSOMETRY

BACKGROUND OF THE INVENTION

1. Field of the Invention

The present invention relates to optical inspection systems, and in particular, to optical systems for inspecting repeating patterns.

2. The Related Art

In the manufacture of integrated circuits (ICs), it is well known to apply a pattern to a substrate by masking a portion of the substrate corresponding to a pattern, and by selectively depositing or removing material on the substrate to form the lines and devices of the IC. Variations in the pattern, including both pattern width and pattern depth, may occur for a variety of reasons. For example, they may occur due to variations in the application of masking material, exposure and development. To achieve the desired accuracy in the ICs, the patterns are often checked during the processing (for end point detection), as well as after completion of circuit processing.

The determination of the shape, depth and width of sub-micron structures on semiconductor wafers can be a difficult task. With sub-micron sized patterns, it has become a common practice to destructively test samples using a scanning electron microscope. This is a time consuming process. It is often desirable to test whether a structure has been formed properly by comparison to a known structure or measurement signature. Such a comparison is useful as an end point detection mechanism, or as an indication of the success of the formation process.

U.S. Pat. No. 4,303,341 to Kleinknecht et al. discusses an inspection method in which a diffraction grating is applied to the substrate being tested. The diffraction grating includes a pattern of evenly spaced lines having a pitch of about 20 micrometers and a line width of 5 micrometers. The substrate is illuminated by a beam of light to form a reflected beam and to form first and second order diffracted beams, having respective intensities $I_1$ and $I_2$. The ratio of $I_2/I_1$ is calculated. The width of the lines is then calculated from the ratio of $I_2/I_1$.

Another method for inspecting repeating patterns has been proposed in Giapis, K. et al., "Use of Light Scattering in Characterizing Reactively Ion Etched Profiles," J. Vac. Sci. Technol. A, Vol. 9, No.3, May 1991, involves the measurement of scattered light intensity. A repeating pattern is illuminated with a laser beam to produce a plurality of diffraction orders. The repeating pattern is spaced widely, with a pitch of approximately 32 micrometers. The large pitch ensures that there are many diffraction orders available for evaluation. The intensity of each diffraction order is then measured. Deviations in the intensity profile are an indication of changes in the repetitive structure.

A disadvantage of the method described above is that, in order to achieve closely spaced diffraction orders, the repeating structures are placed relatively far apart, i.e., 32 micrometers. The patterns on the integrated circuits that are being inspected, however, are closely spaced. This means that the repeating circuit patterns themselves produce very few diffraction orders (when visible wavelengths are used). To overcome this limitation, the inspection method described by Giapis et al. has been performed on test patterns in the form of diffraction gratings on the substrate, instead of using the actual circuit patterns themselves.

Ellipsometry is a different technique that has been used for nondestructively measuring the thicknesses of films, given the complex index of refraction for the film and bare substrate. In ellipsometry, light of a known polarization and incident angle is reflected from the substrate, and relative shifts in the polarization state are measured. In a typical configuration the incident beam is a monochromatic beam that is passed through an adjustable polarizer (e.g., a polarizer and a compensator). The incident beam has both P and S polarizations (parallel to and perpendicular to the plane of incidence, respectively). The reflected beam is passed through an analyzing polarizer, and on to a detector. The adjustable polarizer is adjusted until the light reaching the detector is nulled. The setting of the adjustable polarizer that nulls the detected light determines the field reflection coefficients.

Ellipsometry is useful for analyzing the average film thickness value over an area. Scattering within the reflected beam causes the light from the repeated pattern and from the variations to be intermingled, which achieves averaging. This is a disadvantage, however, if the purpose of the measurement is to detect the variations, as opposed to detecting the average. For spatial resolution over a broad area using ellipsometry, one solution has been to focus the beam on a small portion of the surface and to scan the beam over the surface, one portion at a time. For a large surface this process may involve the scanning of thousands of portions, and may take hours to complete.

Cohn, R. et al., "Dynamic Imaging Microellipsometry; Theory, System Design and Feasibility Demonstration", in Applied Optics/Vol. 27, No. 22, November, 1988 and Cohn, R. and Wagner, J., "Mapping of Surface Film Parameters with Dynamic Imaging Microellipsometry", Quantitative Nondestructive Evaluation, Vol. 8B, discuss imaging ellipsometry devices. In each case, the reflected beam has an angle with respect to the surface normal, and part of the image is out of focus.

SUMMARY OF THE INVENTION

The present invention is embodied in a method and apparatus for inspecting a repeating pattern on an object. An optical inspection system is used to detect variations in the pattern.

The object is illuminated with substantially monochromatic light. A diffracted beam is formed. The diffracted beam has a plurality of polarization components. At least one of the polarization components of the diffracted beam is blocked. Variations in the pattern are detected as light intensity variations in the polarization components that are not blocked.

BRIEF DESCRIPTION OF THE DRAWINGS

FIG. 1 is a block diagram of an exemplary apparatus in accordance with the invention.

FIG. 2 is a diagram showing the polarization state of the incident and diffracted light beams shown in FIG. 1.

FIG. 6 is a block diagram of the fourth exemplary embodiment of the invention.

DESCRIPTION OF THE EXEMPLARY EMBODIMENTS

OVERVIEW

Figure 3:
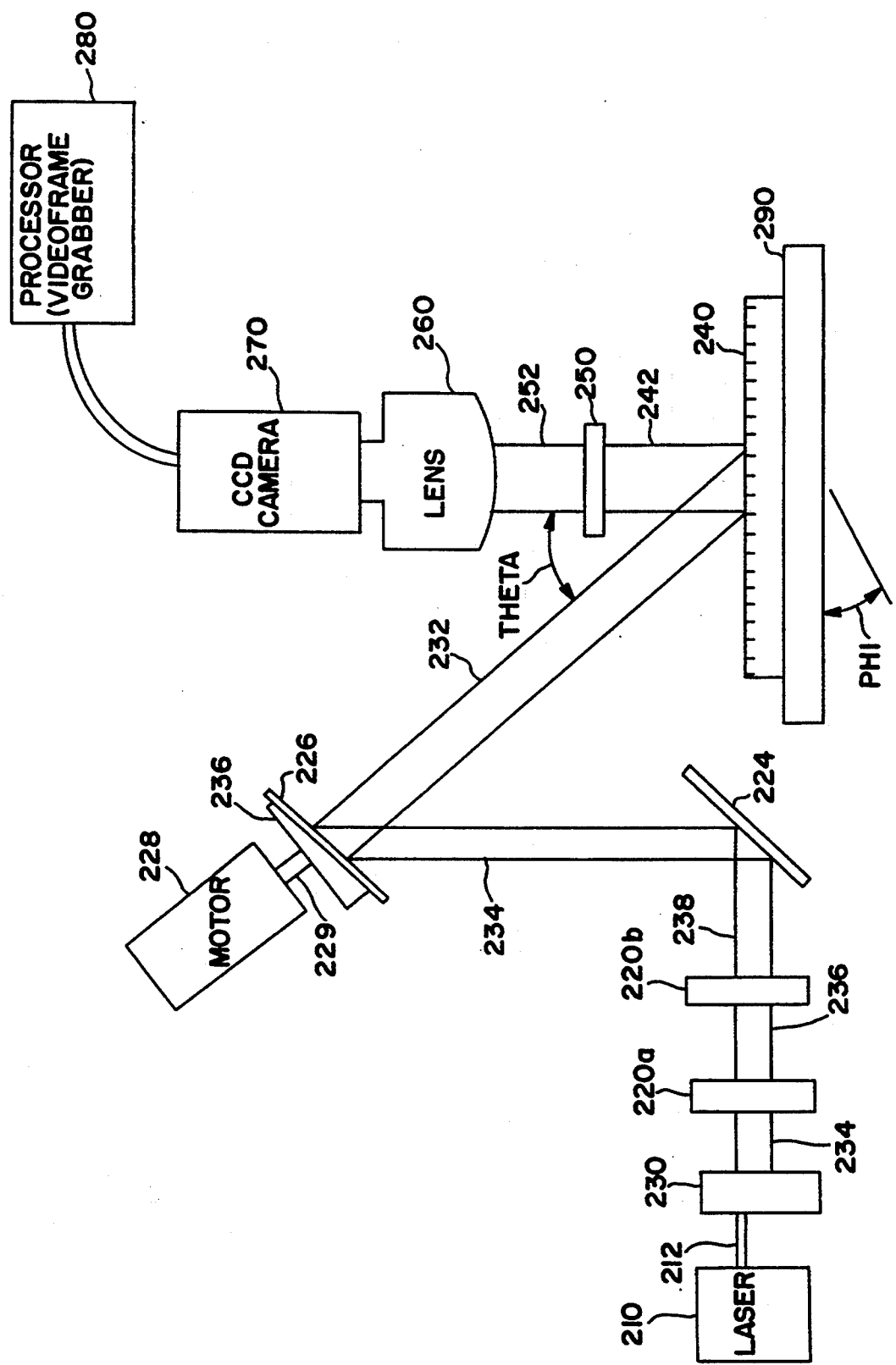
FIG. 3 is a block diagram of a second exemplary embodiment of the invention.

FIG. 1 shows an exemplary apparatus 100 suitable for use in accordance with the present invention. The invention detects variations in a repetitive pattern. The ellipsometric parameters of light diffracted from the repetitive parts 144 (shown in FIG. 2) of a patterned object 140 are measured. Information relating to the repetitive feature 144 shape and size is obtained. Object 140 may be any surface suitable for receiving patterns, such as the top of a silicon wafer or a flat panel display which has printed circuitry. Object 140 may also be a an embedded layer below the surface. For example, a coating of glass or other transparent material may cover the pattern on object 140. The remainder of the discussion below refers to the object as the surface 140. It is understood that the discussion applies equally to inspection of patterns not on the surface.

In accordance with the present invention, ellipsometry may be performed using a single diffracted beam 142. By using the diffracted beam, it is possible to detect deviations within the actual pattern with a fine pitch on the order of a few microns (as opposed to using a test pattern) when using visible wavelengths. In a further exemplary embodiment of the invention, explained below, ellipsometry is performed using four diffracted beams 142.

The repetitive pattern 144 is illuminated using a collimated beam of substantially monochromatic light 112, such as a laser beam, from a light source 110. Beam 112 includes respective components that are parallel to, and perpendicular to, the plane of incidence. Referring again to FIG. 1, beam 112 passes through polarization adjusting means 120. The polarization adjusting means is also referred to herein as elliptical polarizer 120.

The light passing through the polarization adjusting means 120 forms an elliptically polarized beam 122. Elliptically polarized beam 122 passes through a beam expander 130, to cover the field of view. The expanded beam 132 illuminates the surface 140. Due to the repetitive pattern, light scattered from surface 140 adds coherently only in specific directions, producing diffracted beams, such as beam 142. The diffracted beam 142 passes through an analyzing device, also referred to herein as analyzing polarizer 150. The analyzed beam 152 is then provided to detecting means, such as camera lens 160 and camera 170, or a video camera 270, as shown in FIG. 3.

In the first exemplary embodiment shown in FIG. 1, the analyzing polarizer 150 is set to a known, predetermined polarization, for example at an azimuthal angle of 45 degrees relative to the plane of incidence. The polarization of elliptical polarizer 120 is adjusted until polarization of the diffracted beam 142 is linear and is substantially orthogonal to the transmitting axis of linear polarizer 150. This produces a substantially "nulled condition".

As defined herein, the term "nulled condition" means that the average polarization of the diffracted beam 142 is orthogonal to the transmitting axis of the linear analyzing polarizer 150. The analyzed beam 152 is the "null beam" when the "null condition" is present. The nulled condition results in the minimum total illumination reaching the detecting means 170 from analyzed beam 152. The polarization component having the average polarization (corresponding to the repeated pattern) is blocked. The repeated pattern itself appears as dark regions. In fact, if the repeated pattern is perfect and is identical across the field of view, the polarization state of diffracted beam 142 across the field of view is uniform, and is exactly orthogonal to the transmitting axis of linear analyzing polarizer 150. For a perfect repeated pattern, the entire field is blocked. In less-than-perfect patterns, small local deviations from the average polarization are not blocked; these are detected. These local deviations appear as bright areas in the analyzed beam 152. If an image is taken by illuminating the light detecting means 170 with the nulled beam, a "nulled image" is formed. In the nulled image, the repeated pattern is dark, and deviations appear as bright areas.

An advantageous aspect of the present invention is that the angle theta between the surface normal and the light source 110 may be adjusted so that diffracted beam 142 and nulled beam 152 are normal to surface 140. The present invention produces a diffracted beam 142 which is detected by light detecting means 170 parallel to surface 140, such as camera 170. Camera 170 is able to take a focused image of the whole surface, because the image plane is parallel to the surface 140 being imaged. This advantage was not present in prior imaging ellipsometry techniques, which used a reflected beam, having an angle of reflection theta with respect to the surface normal.

It has been determined by the inventor that the ability to detect small deviations in the phase of diffracted beam 142 is enhanced if the elliptical polarizer 120 is adjusted to operate apparatus 100 in a slightly off-null condition. That is, the polarization of diffracted beam 142 is substantially, but not exactly, orthogonal to the polarization of analyzing polarizer 150. This is accompanied by small variations in the complex ellipsometric parameters, as discussed below in greater detail.

When the off-null method described above is used, the average background from the repeating pattern is not black; light is also detected from the repeated pattern. This reduces the contrast of the detected image. It is possible to eliminate the background illumination on the repeated pattern by a differential method. For example, a pair of images may be taken, each image having different off-null conditions. By subtracting the light detected in each image, a differential image is obtained. This allows elimination of the background light. Furthermore, two pairs of images may be taken, to determine the respective variations in light intensity due to variations in each of the respective complex ellipsometric parameters, PSI and DELTA, as discussed below. By selecting the appropriate conditions for each image within a pair, the differential images are obtained with no background illumination from the off-null condition.

Other embodiments of the invention are disclosed herein. In one alternative embodiment (shown in FIG. 3), the incident beam is moved relative to the substrate, so that a larger area is scanned. In another embodiment of the invention, (shown in FIG. 5) there may be a plurality of incident beams, providing multiple independent measurements. These independent beams may vary in angle of incidence and/or wavelength and/or azimuthal angle PHI. If the variations are located in different parts of the pattern, independent measurements using different beams may have different sensitivities to the variations. The plurality of beams may be produced and detected simultaneously or sequentially. In the exemplary embodiment of FIG. 5, the plurality of beams are produced and detected sequentially, so that only one detecting system is needed.

Applications for the invention include, but are not limited to, detecting variations in circuit line width, depth or shape in a system for manufacturing a plurality of identical chips from a single silicon wafer, or a system for manufacturing flat panel displays (including liquid crystal displays). Apparatus in accordance with the invention may be used as an end point detector for the etching of repeated structures such as semiconductor memory chips. In this application, etching is completed when the ellipsometric parameters, which are very sensitive to the repeated structure shape and size, reach a pre-determined value.

DETAILED DESCRIPTION

Referring again to FIG. 1, the first exemplary embodiment of the invention is shown. The repetitive pattern 144 is illuminated using a collimated beam of substantially monochromatic light 112, such as a laser beam, from a light source 110. An alternative source of substantially monochromatic light (not shown) is a source of white light from which a beam is passed through a narrow band pass filter.

In FIG. 1, beam 112 passes through polarization adjusting means 120. Polarization adjusting means 120 can produce a beam having any desired polarization state. Examples of polarization adjusting mechanisms suitable for use in the exemplary embodiments include, but are not limited to, a Babinet compensator, a pair of independently rotatable quarter wave plates, and a pair of variable wave plates (e.g., a liquid crystal type), the first wave plate having an optical axis at 45 degrees to the linear polarization of the laser, and the second wave plate having an optical axis parallel to the linear polarization of the laser. The polarization adjusting means is also referred to herein as elliptical polarizer 120. Beam 132 has both an S polarized component $e_s$ and a P polarized component $e_p$, as shown in FIG. 2. The S polarized component $e_s$ has a polarization perpendicular to the plane of incidence; and the P polarized component $e_p$, has a polarization parallel to the plane of incidence. $e_s$ and $e_p$ are each complex numbers representing the amplitude and phase of each component, respectively.

The light passing through the polarization adjusting means 120 forms an elliptically polarized beam 122. Elliptically polarized beam 122 passes through a beam expander 130, to cover the field of view. The expanded beam 132 illuminates the surface 140. The diffracted beam 142 passes through an analyzing device, such as linear analyzing polarizer 150. In some cases, more than one diffracted beam enter imaging lens 160. In the exemplary embodiment, an aperture 164 may be placed in the Fourier transform plane of the lens 160 to block all except one diffracted beam. The analyzed beam 152 is then provided to detecting means, such as camera lens 160 and camera 170, or a video camera 370, as shown in FIG. 3.

In the first exemplary embodiment shown in FIG. 1, the analyzing polarizer 150 is set to a known, predetermined polarization, for example at an azimuthal angle of 45 degrees relative to the plane of incidence. The polarization of elliptical polarizer 120 is adjusted until polarization of the diffracted beam 142 is linear and is substantially orthogonal to the transmitting axis of linear polarizer 150. This produces a substantially "nulled condition". It will be understood by those of ordinary skill in the art that the adjustment of the elliptical polarizer 120 to null the diffracted beam is analogous to the adjustments made to null the specularly reflected beam when performing ellipsometry on the reflected beam. In a similar manner, it is analytically convenient to characterize the surface in terms of the complex field reflection coefficients obtained by analyzing the diffracted beam, as explained below.

Figure 4:
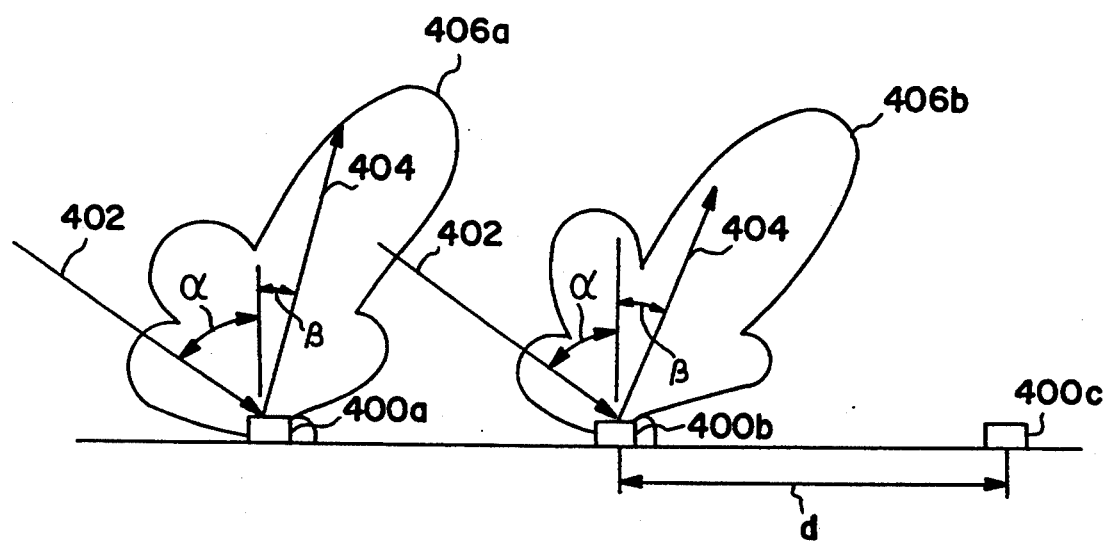
FIG. 4 is a diagram showing the scattering of light by the apparatus shown in FIG. 1.

Referring to FIG. 4, a structure $400a$–$400n$ is shown. Structure $400a$–$400n$ scatters light in all directions. If the repeating components of structure 400 repeat with a close spacing, then the scattering is affected by the interaction of the structures. The scattering function 406$a$ and 406$b$ is referred to as S′, and determines the ratio of the scattered component to the incident component. To compute the diffraction due to the repetitive structures in a given direction, scatter is coherently added from each of the structures $400a$–$400n$. Light only adds coherently at discrete angles. This occurs, at diffraction angle $\beta$ for a beam having an angle of incidence $\alpha$, when $$m*lambda = d*(\sin\alpha + \sin\beta) \tag{1}$$

where:
m = the diffraction order (integer)
lambda = the wavelength
$\alpha$ = angle of incidence
$\beta$ = angle of diffracted beam
d = spacing (pitch) of the repeated pattern Equation (1) considers only one dimension at a time. It is understood by one of ordinary skill in the art that for a two dimensional structure, a similar relationship exists in the orthogonal direction.

This is essentially similar to computations of grating shape on diffraction efficiency. Thus for an allowed diffraction angle of $\beta$, $S'_s(\beta)$ and $S'_p(\beta)$ are monitored. These functions $S'_s(\beta)$ and $S'_p(\beta)$ are functionally similar to the reflection coefficients $r_s$ and $r_p$ insofar as they represent relationships between the light leaving the surface and the incident light. Thus monitoring the ellipticity of the diffracted beam provides a direct measure of the scattering functions $S'_s(\beta)$ and $S'_p(\beta)$. For the two dimensional case, these are referred to for a specific diffracted beam as $d_s$ and $d_p$, respectively.

Referring again to FIG. 2, the diffraction coefficients are defined as follows. Upon diffraction, the ratio of the diffracted parallel (to the plane of incidence) component to the incident parallel component is $d_p$. The ratio of the diffracted perpendicular (to the plane of incidence) component to the incident perpendicular component is $d_s$. In general, $d_p$ and $d_s$ may be complex numbers. The polarization state is now expressed in terms of ellipsometric parameters. The ellipsometric parameters PSI and DELTA are defined as follows:

Tan(PSI) is the change in relative amplitude between $d_p$ (parallel) and $d_s$ (perpendicular), i.e., $$PSI = ARCTAN(|d_p e_p|/|d_s e_s|) \tag{2}$$

where | | is the absolute value function.

DELTA is the change in phase introduced between the parallel and perpendicular components, i.e., $$DELTA = \arg(d_p e_p) - \arg(d_s e_s) \tag{3}$$

where the arg function is the phase angle (argument) of a complex variable, as defined by equation (4).

$$\arg(e^{j\theta}) = \theta \quad (4)$$

where:
j is the square root of $-1$.

Based on the above, the polarization state of the diffracted beam may be defined in terms of PSI and DELTA according to equation (5).

$$PS = |E| * [e^{DELTA*j} * \sin(PSI), \cos(PSI)] \quad (5)$$

where:
PS = Polarization state; and
$|E|^2$ = intensity of the diffracted beam.

The polarization state function PS varies slightly across the field of view, due to the small variations in the size, shape or thickness of the pattern. The analyzer turns these small variations in PS into small intensity variations that are detected by device 170. For a given azimuthal orientation of analyzing polarizer, 150, a unit vector is defined that is aligned with the transmitting axis of the analyzing polarizer. A polarization component of the diffracted beam 142 that coincides with this transmitting axis is passed on, and the remaining polarization component that is orthogonal to the transmitting axis is blocked. This is mathematically equivalent to taking the dot product of the PS vector and the unit vector aligned with the transmitting axis of the analyzing polarizer.

As an example, the inventor has determined that for an exemplary analyzing polarizer 150 having a transmitting axis oriented at an azimuthal angle PHI of 45 degrees, the normalized intensity $i_s$ of the analyzed beam 152, as a fraction of the intensity of diffracted beam 142, is given by equation (6).

$$i_s = [2 - \sin(2*PSI - DELTA) - \sin(2*PSI + DELTA)]/4 \quad (6)$$

where:
$i_s$ = normalized intensity of analyzed beam 152.

The values of PSI and DELTA that minimize the light that reaches detector 170 are referred to herein as $PSI_0$ and $DELTA_0$. For the conditions described above, the null condition occurs when $PSI = PSI_0 = 45$ degrees and $DELTA = DELTA_0 = 0$. This polarization occurs when PSI = 45 degrees, and DELTA = 0 degrees, i.e. when the diffracted beam is linearly polarized orthogonally to the analyzer axis. Thus, for a given point, if the incident polarization is adjusted with elliptical polarizer 120 so that, in combination with the pattern diffraction coefficients ($d_p$ and $d_s$), the above values of PSI and DELTA occur, the beam is nulled at that point. If the entire repeated pattern is uniform, the entire image is black. If there are small deviations in PS at local areas in the image, then the analyzed beam 152 is not nulled at these points. For a non-uniform pattern, the procedure described above does not completely block all of the polarization components of the diffracted beam; the null condition then corresponds to the value that minimizes the total light detected (or the average intensity of light) in the analyzed beam 152.

For the example described above, the intensity of the detected light 152 from area in which PS deviates by a small quantity from the null polarization state varies in accordance with equation (7).

$$i_s = DDELTA^2/4 + DPSI^2 \quad (7)$$

where:
$DDELTA = DELTA - DELTA_0$; and
$DPSI = PSI - PSI_0$.

For a small deviation in the repeating pattern, the change in $i_s$ is difficult to detect, due to the quadratic dependence on a small quantity. Instead, elliptical polarizer 120 may be adjusted to a slightly off-null condition, so that the values of PSI and DELTA deviate by small amounts $DPSI_0$ and $DDELTA_0$ from their respective values $PSI_0$ and $DELTA_0$ at the null condition. $DPSI_0$ and $DDELTA_0$ are chosen to be small, but $DPSI_0$ is larger than the values of DPSI that are to be measured, and $DDELTA_0$ is larger than the values of DDELTA that are to be measured. The image intensity is then given by equation (8).

$$i_s = DDELTA_0 * DDELTA/2 + 2*DPSI_0*DPSI + K \quad (8)$$

where:
K = a constant background intensity.

Although there is a fixed background intensity, K, there is a linear relationship between the variations in the polarization state of the diffracted beam 142, and the intensity of the analyzed beam 152. The effects of light detected due to variations in PSI and due to variations in DELTA are mixed.

When the off-null method described above is used, the light detected varies as a function of both DPSI and DDELTA. It is possible to separate these effects by a differential method. For example, two pairs of images may be taken, each pair having different off-null conditions. The images in each respective pair are subtracted one from another. A respective differential image is obtained from each pair. By selecting the appropriate conditions for each image within a pair, the differential images are obtained with no background illumination from the off-null condition.

Preferably, for the first pair of images, PSI is varied to values of plus and minus $DPSI_0$. For the other pair of images, DELTA is varied to values of plus and minus $DDELTA_0$. The result is that one differential image has the deviations from the repeated pattern illuminated in direct proportion to DPSI; the other differential image has the deviations from the repeated pattern illuminated in direct proportion to DDELTA. The values of PSI and DELTA are then determined.

The differential images may be obtained in a number of ways. Four successive images may be taken, varying the setting of elliptical polarizer 120 for each image. An alternate method involves changing the analyzer state after each image by rotating the analyzing polarizer 150 axis and adding phase retardation such that the four images are obtained with the appropriate conditions. Another alternative (not shown) involves simultaneous imaging using beam splitters, and multiple analyzing and detecting devices. This method requires careful alignment of the imaging devices with respect to one another.

The maximum sensitivity is obtained if $DPSI_0 = 45$ degrees and $DDELTA_0 = 90$ degrees. Then the image signals for small DPSI and DDELTA vary as 2*DPSI and 2*DDELTA, respectively.

In the exemplary embodiment, the light detecting means 170 measures the intensity of the analyzed beam 152 including the background radiation. It does not detect the differential image directly. The subtraction is performed on the detected images to form the differential image. This distinction may be important. When the differential method is used, the light detecting means should have a dynamic range sufficient to include both the background and the small variations that are being measured, even though the background component is discarded later. The further the operating condition is from the null condition, the greater the background intensity, and the smaller the difference between the background and the areas of pattern variation. It may be desirable, for a given detecting means 170, to operate closer to null than the condition described above for maximum sensitivity. The closer the apparatus is to the null condition, the greater the dynamic range available in the differential image.

FIG. 3 shows a second exemplary embodiment of the invention. The second embodiment may be more useful if the object 240 to be inspected is larger than the field of view of the camera lens 260. This embodiment allows imaging using the differential technique described above.

An exemplary light source is a laser beam, such as a HeNe (633 nm wavelength, 10 mW power) or a diode laser (5-50 mW). Other wavelengths may also be useful for specific applications. If the laser includes a polarizing mechanism, then the polarization of beam 212 is oriented to be horizontal. If beam 212 is not polarized, an additional linear polarizing element (not shown) is placed between laser 210 and beam expander 230. Beam expander 230 is selected to nearly fill the field of view of the camera lens 260/CCD videocamera 270 combination. Expanded beam 234 may be, for example, 2-5 mm in size. The expanded beam 234 passes through a first liquid crystal (LC) type variable wave plate 220a, that has an optical axis oriented at 45 degrees to the polarization of beam 234. The beam then passes through a second LC type variable wave plate 220b that has an optical axis oriented at 0 degrees to the polarization of the laser beam 234.

If the first wave plate 220a is set to cause a phase shift of $2PSI_0$, and the second wave plate 220b is set to cause a phase shift of $(90+DELTA_0)$ degrees, then the combined effect of the two waveplates 220a and 220b is that the elliptically polarized beam 238 has ellipsometric parameters $DELTA_0$ and $PSI_0$. Thus a beam 238 having any desired polarization state may be produced.

Beam 238 is directed by a fixed mirror 224 to a rotating mirror 226. Rotating mirror 226 is mounted on a wobble plate 236 attached to a motor 228. The wobble plate 236 is a disk having a front surface that is not parallel to its back surface, but is off by up to a few degrees. When the plate 236 rotates, the beam 232 sweeps out a cone about the motor axis 229. The wobble plate 236 dithers the incident beam 232 in a tight circle about the center of the field of view. By selecting a small dither distance relative to the diameter of beam 232 (e.g., 0.1 to 0.4 times the diameter), intensity variations in the laser beam 212, and variations due to surface roughness on object 240 (due to laser speckle) are averaged out. Preferably, the wobble rate (i.e., motor speed) is several times faster than the camera frame rate. The wobble angle may be smaller than one degree, thereby avoiding any ellipsometric effects due to variation in the incident beam angle.

As in the case of the first exemplary embodiment, values of THETA and PHI are selected so that a diffracted beam normal to the surface of object 240 is formed. The exact values of THETA and PHI depend on the pitch of the repeating pattern.

In this embodiment, the analyzed diffracted beam 252 is detected using a CCD camera 270. The CCD camera image may be captured by a processor 280 using a frame grabber. The processor 280 (or another processor, not shown) controls the data acquisition process. After a sample 240 is positioned on the scanning stage 290, and a first field of view is selected, a null condition is established. This is achieved by systematically changing the ellipsometric parameters $DELTA_0$ and $PSI_0$ of the incident beam 232 until the light 252 reaching camera 270 is minimized. This may be achieved by acquiring successive images and summing all of the pixel values. Alternatively, a single separate photodetector (not shown) may be inserted in front of the camera lens, and the incident beam 232 adjusted until the photodetector's signal value is minimized. Another alternative is to use a beam splitter (not shown) to pass a portion of the diffracted beam to the separate photodetector.

Once the null condition is achieved, a series of four images is acquired, using offsets from the null condition. For one pair of images, PSI is varied to values of plus and minus $DPSI_0$. For the other pair of images, DELTA is varied to values of plus and minus $DDELTA_0$. $DPSI_0$ and $DDELTA_0$ are chosen so that they are greater than the expected DPSI and DDELTA to be measured, but still small enough that the dynamic range of the imaging device is sufficient. The detected pixel values from each image are stored in the memory of processor 280. Two differential images are formed by subtracting the pixel values within each pair of images. The differential images may be displayed, stored, or further analyzed. Additional fields of view may be added to cover a large object 240 by moving the stage 290 and repeating the entire process.

Figure 5:
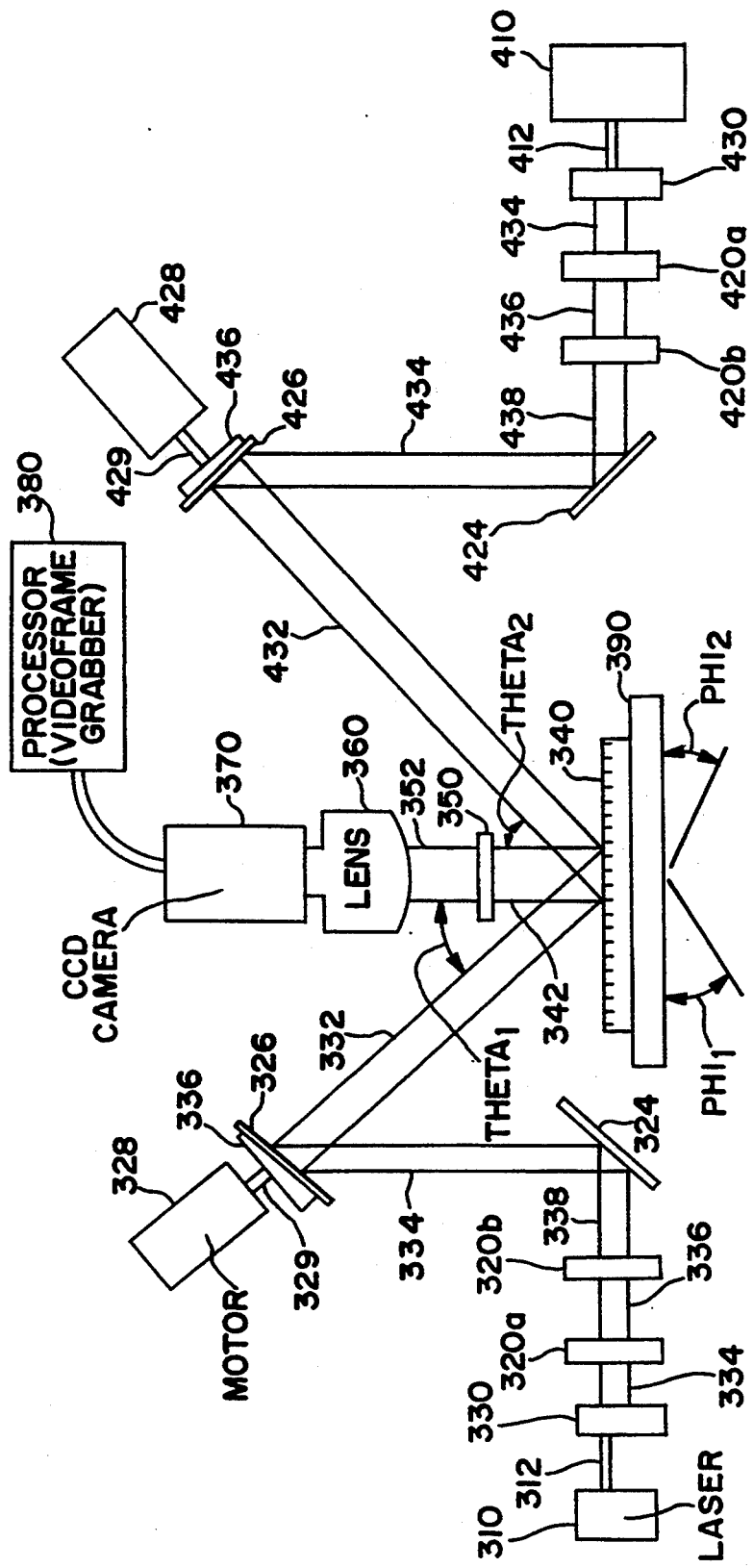
FIG. 5 is a block diagram of a third exemplary embodiment of the invention.

Other variations of the exemplary embodiments may be practiced and are understood by those of ordinary skill in the art. FIG. 5 shows a third exemplary embodiment in which a plurality of incident beams 332 and 432 are formed using respective pluralities of lasers 310 and 410, expanders 330 and 430, waveplates 320a, 320b, 420a and 420b, motors 328 and 428, and mirrors 324, 326, 424 and 426. Each beam forming apparatus is configured to produce a diffracted beam that is normal to the surface of object 340. The images are formed by activating lasers 310 and 410 in succession. For the embodiment of FIG. 5, the lasers 310 and 410 may have the same, or different, wavelengths. The respective angles of incidence $THETA_1$ and $THETA_2$ and azimuthal angles $PHI_1$ and $PHI_2$ may also have the same, or different, values as long as they produce a normally diffracted beam.

The use of monochromatic light is not absolutely essential. A narrow band of wavelengths may be used, such as a collimated white light followed by a narrow band pass filter (not shown). The diffracted beam directions and ellipsometric parameters then vary slightly, as a function of the bandwidth of the light. This type of light may be more desirable if the surface is rough. The use of a band of wavelengths may reduce the speckle effect that is typically observed when a laser beam strikes a surface that has some roughness.

The incident beam may also be slightly divergent or convergent, so long as the sensitivity achieved is satisfactory for the intended measurement and light detecting device. The greater the variation in angle of the incident beam, the more averaging of the ellipsometric measurements will occur, reducing the sensitivity of the measurement. Of course, if the beam diverges too much, then the beam diameter becomes greater than the field of view of the detector.

It is understood by one of ordinary skill in the art that the invention may be practiced using other methods to move the light source relative to the object being inspected.

FIG. 6 shows a further exemplary embodiment of the invention. The purpose of this embodiment is to determine when a process which produces a repetitive pattern is completed, or to accurately control the shape, depth or size parameters of the repetitive pattern 540 produced by such a process.

Laser 510 produces a laser beam 512. The laser beam 512 passes through an elliptical polarizer 520, producing a beam with an elliptical polarization state selected by the computer. The beam is expanded in expander 530 and enters a window 592 in the processing chamber 590. The beam illuminates all, or a portion of, the wafer being processed, which may, for example, be an integrated circuit. A diffracted beam 542 is produced, which exits the process chamber 590 through a second window 594. The diffracted beam 542 passes through an analyzer (linear polarizer) 550 which is oriented at 45 degrees to the s or p planes. The unblocked polarization components 552 are detected by the detector 570.

For the exemplary embodiment of FIG. 6, the computer processor 580 sets the elliptical polarizer 520 such that the diffracted beam 552 is nulled. (i.e. the average polarization of the diffracted beam 542 is blocked). The setting of the elliptical polarizer 520 which produces the nulled beam 552 is related to the polarization state of the diffracted beam 542, as given by the diffraction coefficients, dp and ds. The setting of polarizer 520 changes with time as the process continues to change the shape, size or depth of the repetitive pattern (whichever is used as the predetermined end detection criterion). Processor 580 monitors the polarization state of the diffracted beam to determine when the predetermined criterion representing an end point of a process is met.

By repeating the nulling process at frequent time intervals, the diffraction coefficients may be monitored, and the process may be terminated at an identical point for each wafer 540 processed, based on reaching a predetermined shape or depth to the repetitive pattern. The diffraction coefficients may be determined by operating the apparatus 500 in a number of manners that are familiar to those of ordinary skill in the art of ellipsometry. For example, the elliptical polarizer 520 may be changed in a continuous fashion, producing a sinusoidal signal variation at the detector 570. This sinusoidal signal may be analyzed by noting its phase and amplitude to determine the diffraction coefficients.

Although the exemplary embodiments are described in terms of reflecting systems, other variations of the exemplary embodiments are contemplated for inspecting samples that form a transmitted diffracted beam.

It is understood by one of ordinary skill in the art that many variations of the embodiments described herein are contemplated. While the invention has been described in terms of exemplary embodiments, it is contemplated that it may be practiced as outlined above with modifications within the spirit and scope of the appended claims.

What is claimed:

1. In an optical system for inspecting an object, a method of inspecting a repeating pattern on the object, comprising the steps of:
   (a) illuminating the object with substantially monochromatic light;
   (b) forming a diffracted beam from the substantially monochromatic light, the diffracted beam comprising a plurality of diffracted beam components, each having a respective polarization state;
   (c) blocking at least one of the diffracted beam components;
   (d) detecting the diffracted beam components that are not blocked; and
   (e) determining a polarization state of the diffracted beam based on the diffracted beam components that are not blocked.

2. A method in accordance with claim 1, wherein step (d) includes detecting at least one of variations in size in the repeating pattern and variations in shape in the repeating pattern.

3. A method in accordance with claim 1, wherein step (c) includes the step of adjusting at least one of an elliptical polarizer and an analyzing polarizer.

4. In an optical system for inspecting an object, a method of inspecting a repeating pattern on the object, comprising the steps of:
   (a) illuminating the object with substantially monochromatic light;
   (b) forming a diffracted beam from the substantially monochromatic light, the diffracted beam comprising a plurality of diffracted beam components, each having a respective polarization state, the diffracted beam having an average polarization;
   (c) blocking a diffracted beam component having a polarization state equal to the average polarization, to substantially null the diffracted beam; and
   (d) detecting the diffracted beam components that are not blocked.

5. A method according to claim 4, further comprising:
   (e) detecting at least one of variations in size in the repeating pattern and variations in shape in the repeating pattern.

6. A method in accordance with claim 5, further comprising the steps of:
   changing the wavelength of the substantially monochromatic light;
   repeating steps (a) through (d); and
   detecting additional variations in the pattern that differ from the variations detected in step (e).

7. A method in accordance with claim 5, wherein the substantially monochromatic light has an angle of incidence relative to a direction that is normal to the object and an azimuthal angle in a plane of the object, the method further comprising the steps of:
   changing at least one of the group consisting of the angle of incidence and the azimuthal angle;
   repeating steps (a) through (d); and
   detecting additional variations in the pattern that differ from the variations detected in step (e).

8. A method in accordance with claim 4, wherein step (b) includes the step of forming the diffracted beam normal to the object.

9. A method in accordance with claim 8, further comprising the step of:
   forming an image of the pattern from the diffracted beam.

10. A method in accordance with claim 4, wherein step (b) includes the step of elliptically polarizing the substantially monochromatic light.

11. A method in accordance with claim 1, wherein a plurality of diffracted beams are produced from the substantially monochromatic light, further comprising the step of:
blocking at least one of the plurality of diffracted beams so that at most one of the diffracted beams is detected by the light detecting means.

12. In an optical system for inspecting an object, having a source of substantially monochromatic light, an elliptical polarizer positioned between the light source and the object, light detecting means, and an analyzing polarizer positioned between the object and the light detecting means; a method of inspecting a repeating pattern on an object to detect variations in the pattern, comprising the steps of:
(a) illuminating the object with substantially monochromatic light from the light source, the monochromatic light including a first light component having a polarization state that is parallel to a plane of incidence of the monochromatic light and a second light component having a polarization state that is perpendicular to the plane of incidence;
(b) forming, from the substantially monochromatic light, a diffracted beam that is incident upon the light detecting means, the diffracted beam comprising a plurality of diffracted beam components, each diffracted beam component having a respective polarization state;
(c) adjusting at least one of the elliptical polarizer and the analyzing polarizer to block at least one of the diffracted beam components; and
(d) detecting variations in the pattern as light intensity variations in the diffracted beam components that are not blocked.

13. In an optical system for inspecting an object, a method of inspecting a repeating pattern on the object, comprising the steps of:
(a) illuminating the object with substantially monochromatic light including a first light component having a polarization state that is parallel to a plane of incidence of the substantially monochromatic light and a second light component having a polarization state that is perpendicular to the plane of incidence;
(b) forming a diffracted beam from the substantially monochromatic light, the diffracted beam comprising a plurality of diffracted beam components, each diffracted beam component having a respective polarization state;
(c) blocking at least one of the diffracted beam components;
(d) detecting the diffracted beam components that are not blocked; and
(e) determining a polarization state of the diffracted beam based on the diffracted beam components that are not blocked.

14. A method in accordance with claim 13, further comprising the step of monitoring the polarization state of the diffracted beam for determining when a process has reached an end point.

15. An optical system for inspecting an object, comprising:
means for illuminating the object with substantially monochromatic light including a first light component having a polarization state that is parallel to a plane of incidence of the substantially monochromatic light and a second light component having a polarization state that is perpendicular to the plane of incidence;
means for forming, from the substantially monochromatic light, a diffracted beam that emanates from the object, the diffracted beam comprising a plurality of diffracted beam components, each diffracted beam component having a respective polarization state, the diffracted beam having an average polarization;
means for blocking a diffracted beam component that is equal in polarization to the average polarization, thereby substantially nulling the diffracted beam; and
means for detecting the diffracted beam components that are not blocked.

16. An optical system as claimed in claim 15, wherein the blocking means include an analyzing polarizer, the analyzing polarizer having a transmitting axis that is substantially orthogonal to an average polarization of the diffracted beam, the analyzing polarizer being positioned between the object and the detecting means.

17. An optical system as claimed in claim 16, wherein the analyzing polarizer is a linear polarizer.

18. An optical system as claimed in claim 15, wherein the forming means include an elliptical polarizer.

19. An optical system as claimed in claim 15, further comprising:
means for moving the light source relative to the object to inspect a larger area.

20. An optical system as claimed in claim 15, wherein the light detecting means include one of the group consisting of a photodetector, a camera and a videocamera.

21. Apparatus according to claim 4, wherein step (d) includes detecting a first diffracted beam component that is parallel to the plane of incidence and a second diffracted beam component that is perpendicular to the plane of incidence.

22. A method according to claim 15, further comprising means for determining a polarization state of the diffracted beam based on the diffracted beam components that are not blocked.

23. In an optical system for inspecting an object, a method of inspecting a repeating pattern on the object, comprising the steps of:
(a) illuminating the object with substantially monochromatic light;
(b) forming a diffracted beam from the substantially monochromatic light, the diffracted beam comprising a plurality of diffracted beam components, each having a respective polarization state, the diffracted beam having an average polarization;
(c) blocking at least one of the diffracted beam components;
(d) detecting the diffracted beam components that are not blocked;
(e) forming an additional diffracted beam having an additional average polarization and a plurality of additional diffracted beam components, the additional average polarization being different from the average polarization of the diffracted beam formed in step (b);
(f) blocking one of the additional diffracted beam components;
(g) detecting light intensity variations in the additional diffracted beam; and
(h) subtracting the light detected during step (g) from the light detected during step (d), thereby to detect variations in the repeating pattern.

* * * * *